(12) United States Patent
Wilson et al.

(10) Patent No.: US 7,300,430 B2
(45) Date of Patent: Nov. 27, 2007

(54) MULTI-LUMEN CATHETER WITH ATTACHABLE HUB

(75) Inventors: Jon S. Wilson, Winston-Salem, NC (US); Carl M. Fleming, Palm City, FL (US); Kenneth T. Cassidy, Mocksville, NC (US); Ronald D. Boyd, Statesboro, GA (US); Gary S. Fleming, Palm City, FL (US)

(73) Assignee: Arrow International, Inc., Reading, PA (US)

( * ) Notice: Subject to any disclaimer, the term of this patent is extended or adjusted under 35 U.S.C. 154(b) by 489 days.

(21) Appl. No.: 10/251,411

(22) Filed: Sep. 20, 2002

(65) Prior Publication Data

US 2006/0276773 A1 Dec. 7, 2006

Related U.S. Application Data

(63) Continuation-in-part of application No. 10/086,033, filed on Feb. 28, 2002, which is a continuation of application No. 09/769,052, filed on Jan. 24, 2001.

(51) Int. Cl.
*A61M 25/00* (2006.01)

(52) U.S. Cl. .................... 604/523; 604/533; 604/43
(58) Field of Classification Search .............. 604/523, 604/533, 534, 537, 535, 539, 284, 264, 905, 604/43, 177, 29
See application file for complete search history.

(56) References Cited

U.S. PATENT DOCUMENTS

| | | | |
|---|---|---|---|
| 4,134,402 A | 1/1979 | Mahurkar | |
| 4,299,228 A | 11/1981 | Peters | |
| 4,327,722 A | 5/1982 | Groshong et al. | |
| 4,432,752 A | 2/1984 | Marlon | |
| 4,453,928 A | 6/1984 | Steiger | |
| RE31,873 E * | 4/1985 | Howes | 128/674 |
| 4,543,087 A | 9/1985 | Sommercorn et al. | |
| 4,568,329 A | 2/1986 | Mahurkar | |
| 4,619,643 A | 10/1986 | Bai | |
| 4,623,327 A | 11/1986 | Mahurkar | |
| 4,643,711 A * | 2/1987 | Bates | 604/4 |
| 4,675,004 A * | 6/1987 | Hadford et al. | 604/44 |
| 4,681,122 A * | 7/1987 | Winters et al. | 128/736 |
| 4,682,978 A * | 7/1987 | Martin | 604/43 |
| 4,692,141 A | 9/1987 | Mahurkar | |
| 4,772,268 A * | 9/1988 | Bates | 604/174 |
| 4,772,269 A | 9/1988 | Twardowski et al. | |
| 4,808,155 A | 2/1989 | Mahurkar | |
| 4,832,687 A | 5/1989 | Smith | |
| 4,895,561 A * | 1/1990 | Mahurkar | 604/43 |
| 5,053,003 A * | 10/1991 | Dadson et al. | 604/28 |
| 5,053,004 A | 10/1991 | Markel et al. | |
| 5,053,023 A * | 10/1991 | Martin | 604/280 |
| 5,059,170 A * | 10/1991 | Cameron | 604/43 |
| 5,106,368 A | 4/1992 | Uldall et al. | |
| 5,129,891 A * | 7/1992 | Young | 604/283 |

(Continued)

OTHER PUBLICATIONS

Believed to be an unpublished sketch of a conception by Dr. John Frusha; date of sketch believed to be Jun. 24, 1997.

(Continued)

*Primary Examiner*—Frederick C. Nicolas
(74) *Attorney, Agent, or Firm*—Amster, Rothstein & Ebenstein LLP

(57) ABSTRACT

The present invention is a multi-lumen catheter assembly having a selectively attachable hub including a multi-lumen catheter tube that has a proximal portion and a distal portion and a hub assembly that has a proximal portion and a distal portion, whereby the distal portion of the catheter tube is selectively attachable to the proximal portion of the hub assembly after subcutaneous insertion of the proximal portion of the catheter tube into a patient.

13 Claims, 8 Drawing Sheets

U.S. PATENT DOCUMENTS

| | | | |
|---|---|---|---|
| 5,171,227 A | | 12/1992 | Twardowski |
| 5,190,520 A | * | 3/1993 | Fenton, Jr. et al. ............ 604/29 |
| 5,312,337 A | | 5/1994 | Flaherty et al. ............... 604/93 |
| 5,322,519 A | | 6/1994 | Ash |
| 5,334,185 A | | 8/1994 | Giesy et al. |
| 5,342,386 A | * | 8/1994 | Trotta ......................... 606/194 |
| 5,360,397 A | * | 11/1994 | Pinchuk ...................... 604/27 |
| 5,380,276 A | * | 1/1995 | Miller et al. .................. 604/28 |
| 5,399,168 A | * | 3/1995 | Wadsworth, Jr. et al. ... 604/175 |
| 5,405,320 A | | 4/1995 | Twardowski et al. |
| 5,405,341 A | | 4/1995 | Martin |
| 5,417,668 A | * | 5/1995 | Setzer et al. ............... 604/263 |
| 5,423,768 A | * | 6/1995 | Folden et al. ............... 604/200 |
| 5,431,661 A | | 7/1995 | Koch |
| 5,472,432 A | * | 12/1995 | Martin ........................ 604/248 |
| 5,509,897 A | * | 4/1996 | Twardowski et al. ......... 604/43 |
| 5,558,635 A | * | 9/1996 | Cannon ........................ 604/49 |
| 5,599,328 A | * | 2/1997 | Stevens ..................... 604/533 |
| 5,624,413 A | * | 4/1997 | Markel et al. .............. 604/280 |
| 5,632,729 A | * | 5/1997 | Cai et al. ..................... 604/93 |
| 5,637,102 A | * | 6/1997 | Tolkoff et al. .............. 604/283 |
| 5,685,867 A | | 11/1997 | Twardowski |
| 5,704,915 A | | 1/1998 | Melsky et al. .............. 604/175 |
| 5,718,678 A | * | 2/1998 | Fleming, III ................. 604/43 |
| 5,718,692 A | | 2/1998 | Schon et al. |
| 5,743,873 A | * | 4/1998 | Cai et al. ..................... 604/93 |
| 5,772,643 A | * | 6/1998 | Howell et al. .............. 604/283 |
| 5,776,111 A | * | 7/1998 | Tesio .......................... 604/264 |
| 5,797,869 A | * | 8/1998 | Martin et al. .................. 604/43 |
| 5,807,311 A | * | 9/1998 | Palestrant ..................... 604/28 |
| 5,876,366 A | | 3/1999 | Dykstra et al. |
| 5,944,732 A | | 8/1999 | Raulerson et al. |
| 5,947,953 A | | 9/1999 | Ash et al. |
| 5,989,206 A | * | 11/1999 | Prosl et al. ..................... 604/5 |
| 5,989,213 A | * | 11/1999 | Maginot ....................... 604/28 |
| 6,001,079 A | | 12/1999 | Pourchez |
| 6,033,382 A | | 3/2000 | Basta |
| 6,074,374 A | * | 6/2000 | Fulton ........................ 604/249 |
| 6,086,555 A | | 7/2000 | Eliasen et al. ................ 604/93 |
| 6,113,572 A | * | 9/2000 | Gailey et al. ................. 604/93 |
| 6,156,016 A | * | 12/2000 | Maginot ..................... 604/264 |
| 6,190,349 B1 | * | 2/2001 | Ash et al. ..................... 604/43 |
| 6,190,371 B1 | * | 2/2001 | Maginot et al. ............ 604/523 |
| 6,206,849 B1 | * | 3/2001 | Martin et al. ................. 604/43 |
| 6,293,927 B1 | * | 9/2001 | McGuckin, Jr. ............ 604/266 |
| 6,342,120 B1 | | 1/2002 | Basta |
| 6,428,513 B1 | * | 8/2002 | Abrahamson ............... 604/174 |
| 6,585,705 B1 | | 7/2003 | Maginot et al. |
| 6,638,242 B2 | | 10/2003 | Wilson et al. |
| 6,682,498 B2 | | 1/2004 | Ross |
| 6,682,519 B1 | | 1/2004 | Schon |
| 6,719,749 B1 | | 4/2004 | Schweikert et al. |
| 6,749,574 B2 | | 6/2004 | O'Keefe |
| 6,858,019 B2 | | 2/2005 | McGuckin, Jr. et al. |
| 2001/0041857 A1 | * | 11/2001 | Sansoucy ..................... 604/33 |
| 2003/0088213 A1 | * | 5/2003 | Schweikert et al. ........ 604/177 |
| 2003/0153898 A1 | | 9/2003 | Schon et al. |

OTHER PUBLICATIONS

Twardowski, TJ, Opti–Flow Catheter Tip Translocation From the Right Atrium to the Right Atrium to the Right Ventrical, 2001; 2: pp. 17–19, Wichtig Editore, 2001.

Bio–Flex Tesio Catheters, Sales Brochure, Rev. D, Apr. 2006.

Schon Chronic Dialysis Catheter, Sales Brochure, Rev. D, Apr. 2005.

Pourchez Retro and Pourchez Xpresso, Sales Brochure.

Response to Interrogatory No. 3 by Defendant Spire Biomedical, Inc. in the matter of Arrow International, Inc. et al. v. Spire Biomedical, Inc., Civil Action No.: 05–10671 (DPW) U.S. Dist. Ct. Dist. of Massachusetts.

Wheeler, R.A. et al., Retrograde Tunnel: A Method for the Fixation of Long–Term Pediatric Central Lumen Catheters, Journal of Parenteral and Enteral Nutrition, Jan.–Feb. 1991; pp. 114–115; vol. 14–No. 1, American Society for Parenteral and Enteral Nutrition, U.S.

Wheeler, R.A. et al., Retrograde Tunnel: A Method for the Fixation of Central Venous Catheters in the Military Environment, Journal of the Royal Navy Medical Service, Summer 1991; pp. 75–77; vol. 77, United Kingdom.

Pourchez Retro Instructions for Use.

Pourchez Expresso Product Label dated Feb. 5, 2002.

Twardowski, Z.J. Vascular Access for Hemodialysis: A Historical Perspective for Intravenous Catheters, The Journal for Vascular Access, 2000, 1: 42–45, Wichtig Editore 2000.

Canaud, B., et al., Permanent Twin Catheter: A Vascular Access Option of Choice for Haemodialysis in Elderly Patients, Nephrology Dialysis Transplantation, 1998, 13 [Suppl 7]: 82–88; European Renal Association–European Dialysis and Transplant Association, 1998.

Instructions for Use (Copyright Dated 1990) for Polycath Polyurethane Central Venous Catheter; believed to have been packaged with product believed to have been sold in the United States before Jan. 2000 and related marketing materials.

Instructions for Use (Copyright Dated 1992) for FloLock Single Lumen Bi–directional Valved Catherter; believed to have been packaged with product believed to have been sold in the United States before Jan. 2000.

Instructions for Use (not dated) for Infuse–a–Cath Polyurethane Central Venous Catheter; believed to have been packaged with product believed to have been sold in the United States before Jan. 2000.

Pictures of device believed to be partial sample of a product believed to have been sold in the United States before Jan. 2000 with the Polycath and/or Infuse–a–Cath Instructions for Use.

Copending U.S. Appl. No. 10/231,748; entitled Double Y–Shaped Multi–Lumen Catheter with Selectively Attacheble Hubs, filed Aug. 30, 2002.

Copending U.S. Appl. No. 10/231,748; entitled Multi-Lumen Catheter with Integrated Connector, filed Aug. 30, 2002.

Copending U.S. Appl. No. 10/251,384; Apparatus and Method for Reverse Tunneling a Multi–Lumen Catheter in a Patient, filed Sep. 20, 2002.

Copending U.S. Appl. No. 10/612,532; entitled Multi-Lumen Catheter with Attachable Hub, filed Jul. 1, 2003.

Abandoned U.S. Appl. No. 10/086,033; entitled Multi-Lumen Catheter with Attacheble Hub, filed Jan. 24, 2001.

Polycath Polyurethane Cantral Venous Catheter, Instructions for Use. Dated 1992.

Flolock Single Lumen Bi–directional Valved Catheter, Instructions for Use. Dated 1992.

Infuse–a–Cath Polyurethance Central Venous Catheter, Instructions for Use. Not Dated.

* cited by examiner

US 7,300,430 B2

MULTI-LUMEN CATHETER WITH ATTACHABLE HUB

RELATED APPLICATIONS

This is a continuation-in-part of pending U.S. patent application Ser. No. 10/086,033, filed Feb. 28, 2002, which is a continuation of application Ser. No. 09/769,052 filed Jan. 24, 2001.

FIELD OF THE INVENTION

The present invention relates generally to medical instrumentation and more specifically to a multi-lumen catheter with a selectively attachable hub assembly that allows the catheter tip to be positioned accurately prior to subcutaneous reverse tunneling.

BACKGROUND OF THE INVENTION

Catheters, generally, are hollow, flexible tubes for insertion into a body cavity, duct, or vessel to allow the passage of fluids or distend a passageway. Catheters are often used for temporary or long-term dialysis treatment. Dialysis treatment provides for blood to be withdrawn from the patient, purified, and then returned to the patient. Thus, in dialysis treatment, catheters are used to allow passage of a patient's blood into and out of the patient's body. For optimal performance during dialysis treatment, the catheter tips, both in-flow and out-flow, should be placed in close proximity to the heart. Typically, medical personnel use either a double lumen catheter or two single lumen catheters. Both types, however, present certain deficiencies.

While double lumen catheters (e.g., U.S. Pat. No. 4,895, 561) allow for a single venous insertion of the catheter into the desired vein, double lumen catheters typically do not provide for accuracy of catheter tip placement. Due to differences among patients, optimal tip position varies from patient to patient. Non-optimal tip position may significantly lower flow values, resulting in less effective dialysis treatment. For current double lumen catheters, a physician must make an estimate regarding the appropriate catheter tube length prior to beginning the procedure of catheterization. Then, a subcutaneous tunnel is made from the preferred end position of the hub assembly, namely, away from the neck of the patient in order to allow for more convenient access to the dialysis treatment equipment. The double lumen catheter tube is then tunneled forwardly into the patient's vein. The initial estimate and subsequent forward tunneling may result in less than optimal tip placement.

With the use of two independent catheters (e.g., U.S. Pat. Nos. 5,776,111 and 5,624,413) the problem of tip placement is addressed. The hub assembly of each catheter is removable from the tube and tip portion of the catheter, thereby allowing the catheter tip to be placed directly into the vein and advanced into the desired position. Then, the proximal end of the catheter can be reversed tunneled and trimmed to a desired length. Thereafter, the hub assembly is attached. Deficiencies, however, exist in this method of catheterization as well. One problem associated with this method is that this method requires two separate venous insertions, namely, two tunnels and two of each accessory instrument used for the procedure. Therefore, there is increased surgical time required to place two catheters, there are two wound entry sites which doubles the risk of post-surgical infection, and the two catheters together are significantly larger in diameter than one double lumen catheter.

SUMMARY OF THE INVENTION

The present invention is a double lumen catheter with a selectively detachable hub assembly that allows the catheter tip to, be positioned accurately within a patient's vein prior to subcutaneous tunneling. The distal end of the catheter tube is not permanently attached to the hub assembly. Therefore, the catheter may be reverse tunneled after the tips have been positioned.

The hub assembly includes at least two cannulae that coordinate and correspond to the at least two lumen at the distal end of the catheter tube. Once the hub assembly is connected to the catheter tube so as to provide fluid communication therebetween, preferably, a connection cover and a malleable compression sleeve are secured into place. Preferably, the connection cover is threaded to mate with a threaded connection on the hub assembly. The connection cover and the compression sleeve together create force to prevent inadvertent separation of the catheter tube from the hub assembly while maintaining the diameter of the lumens throughout the connection area.

These and other aspects of the present invention as disclosed herein will become apparent to those skilled in the art after a reading of the following description of the preferred embodiments and drawings. The description and drawings are for the purpose of describing a preferred embodiment of the invention and are not intended to limit the present invention.

DETAILED DESCRIPTION OF THE PREFERRED EMBODIMENT

For the purposes of the following description and the claims appended hereto, the relative term "proximal" refers to those portions of a catheter and those portions of components of the catheter which are nearest the insertion end of the catheter, that is, the end of the catheter that as it is inserted into an area of a patient's body being catheterized, such as a blood vessel. Conversely, the relative term "distal" refers to those portions of a catheter and those portions of components of the catheter which are farthest from the insertion end of the catheter.

Figure 1:
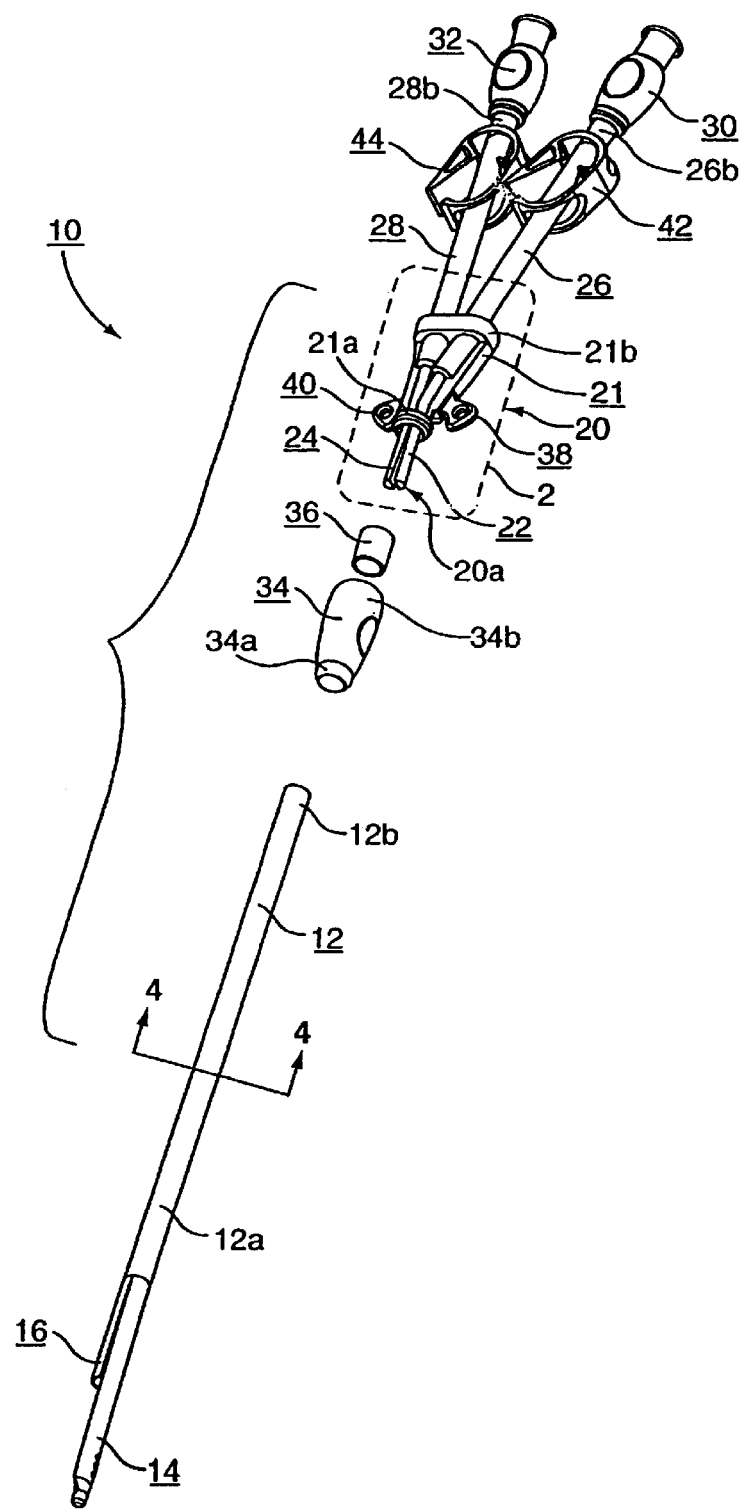
FIG. 1 is an exploded, perspective view of a multi-lumen catheter assembly of the present invention.

As shown in the Figures, the present invention is a multi-lumen catheter assembly 10 having a selectively attachable hub assembly 20. As shown in FIG. 1, a multi-lumen catheter tube 12 is formed with a proximal portion 12a and a distal portion 12b. The distal portion 12b of the catheter tube 12 is selectively attachable to the proximal portion 20a of the hub assembly 20. In this manner, the hub assembly 20 may be attached to the catheter tube 12 after insertion of the proximal portion 12a of the catheter tube, including tips 14 and 16, into a patient.

Figure 2:
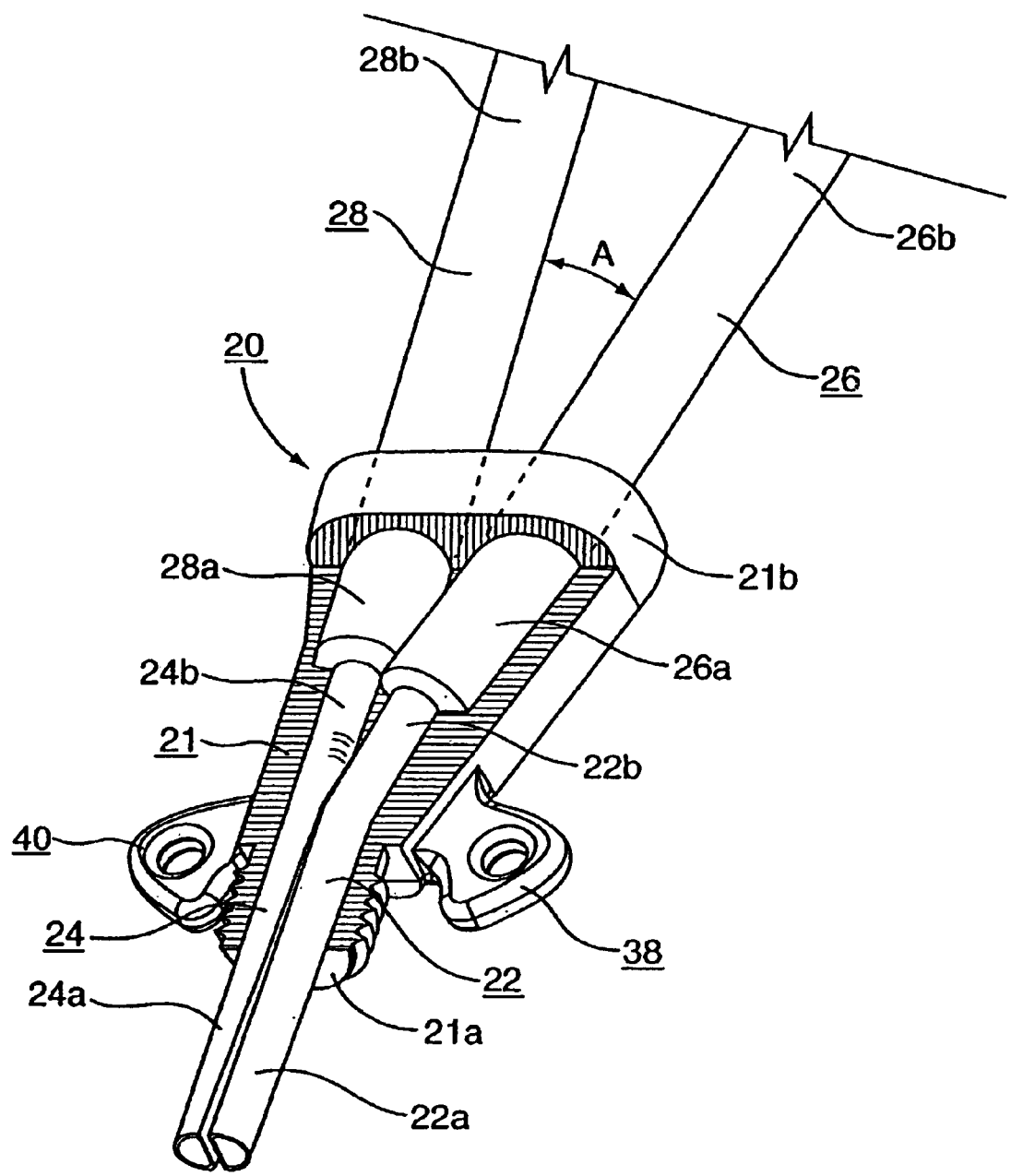
FIG. 2 is an enlarged, exploded, perspective view of a hub assembly of the multi-lumen catheter assembly of the present invention, including a first cross-sectional view of the hub body.

As illustrated in FIG. 2, preferably, the hub assembly 20 has a first cannula 22 and a second cannula 24. Each of the cannulae has a proximal portion 22a and 24a, respectively, and a distal portion 22b and 24b, respectively. Further, each cannulae 22 and 24 has an associated extension tube, 26 and 28 respectively. Each of the extension tubes 26 and 28 has a proximal portion 26a and 28a, respectively, and a distal portion 26b and 28b, respectively. Each of the extension tubes 26 and 28 are in fluid communication with the first cannula and second cannula 24, respectively, through appropriate connection of respective proximal and distal portions, namely connection of the cannulae distal portions 22b and 24b with extension tube proximal portions 26a and 28a, respectively. While the drawings depict the hub assembly with two cannulae, any appropriate configuration and number of cannulae should be considered within the scope of the present invention.

As shown in FIG. 2, preferably, the hub body 21 is formed to maintain the angle A between the first extension tube 26 and the second extension tube 28 at about 15 degrees. This angle is preferred based upon the necessity for connecting the catheter assembly 10 to the fluid conveying device, e.g., dialysis equipment.

Returning to FIG. 1, the hub assembly 20 further includes a first connector 30 and a second connector 32. The connectors 30, 32 may be luer fittings, as are known in the art. The first connector 30 is securely attached to the distal portion of the first extension tube 26b and the second connector 32 is securely attached to the distal portion of the second extension tube 28b. Each of the connectors 30, 32 preferably is attachable to a fluid conveying device (not shown), such as dialysis equipment, as is known in the art. Thus, the respective cannulae 22 and 24 are in fluid communication with extension tubes 26 and 28, respectively. Therefore, the cannulae 22, 24 provide for respective in-flow and out-flow operation of the fluid conveying device.

Each extension tube 26 and 28 has a clamp, 42 and 44, respectively, for clamping the extension tubes 26 and 28 when the catheter assembly 10 is not connected to a fluid conveying device.

The hub body 21 has two suture wings 38 and 40, which can be used to suture the catheter assembly 10 to the patient to maintain the position of the catheter assembly 10 after insertion into the patient.

Figure 3:
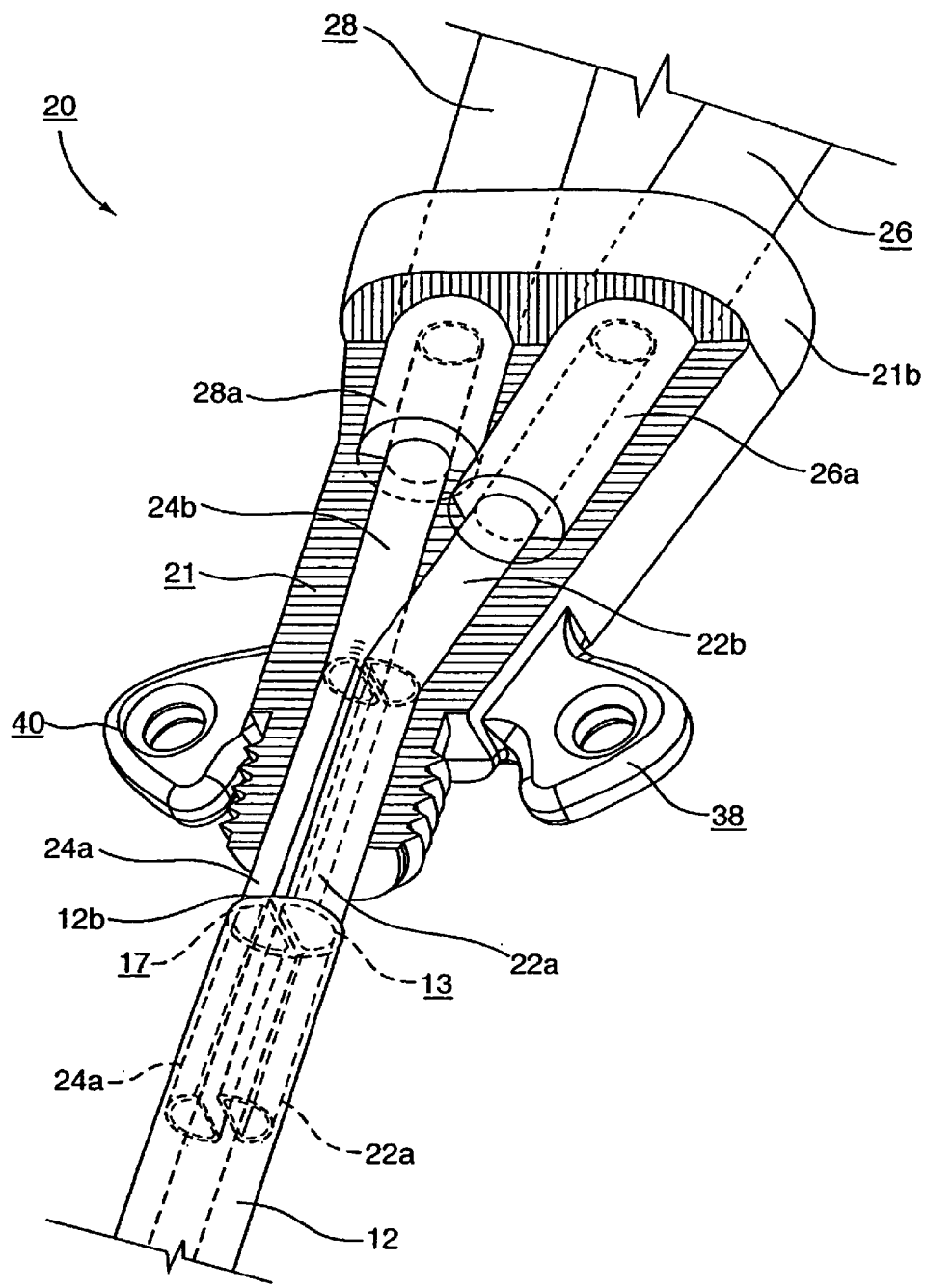
FIG. 3 is an enlarged, exploded, perspective view of the hub assembly and distal portion of a catheter tube of the present invention, including the first cross-sectional view of the hub body.

As shown in FIG. 3, the hub assembly 20 preferably is formed such that each proximal end of the cannulae 22a and 24a has a generally D-shaped cross-section. Preferably, the distal portion of each of the cannulae 22b and 24b has a generally O-shaped cross-section. As such, preferably, the proximal portions 26a and 28a of each of the extension tubes 26 and 28a have a generally O-shaped cross-section and are configured to receive the distal portions 22b and 24b of the respective first and second cannulae 22 and 24. The shape and cross-section configuration of the cannulae 22, 24 the extension tubes 26, 28 and the lumens 13, 17 of the catheter tube 12, may be varied, and, thus, the scope of the present invention should not be limited to the above-described preferred configuration.

Preferably, a hub body 21 is formed around the proximal portions of each of the extension tubes and the distal portions of each of the cannulae. As illustrated in FIG. 2, the hub body 21 provides for protection against disconnection of the several connections between cannulae 22, 24 and extension tubes 26, 28. Further, the hub body 21 provides a structure for connection with the catheter tube 12. More specifically, hub body 21 has a proximal portion 21a and a distal portion 21b. As previously mentioned, the hub body 21 is selectively attachable to the distal portion 12b of the catheter tube 12 so as to provide fluid communication between the respective cannulae 22 and 24 (via proximal portions of the cannulae 22a and 24a) with the lumens 13 and 17, respectively, of the catheter tube 12, which is discussed in more detail below.

Figure 4:
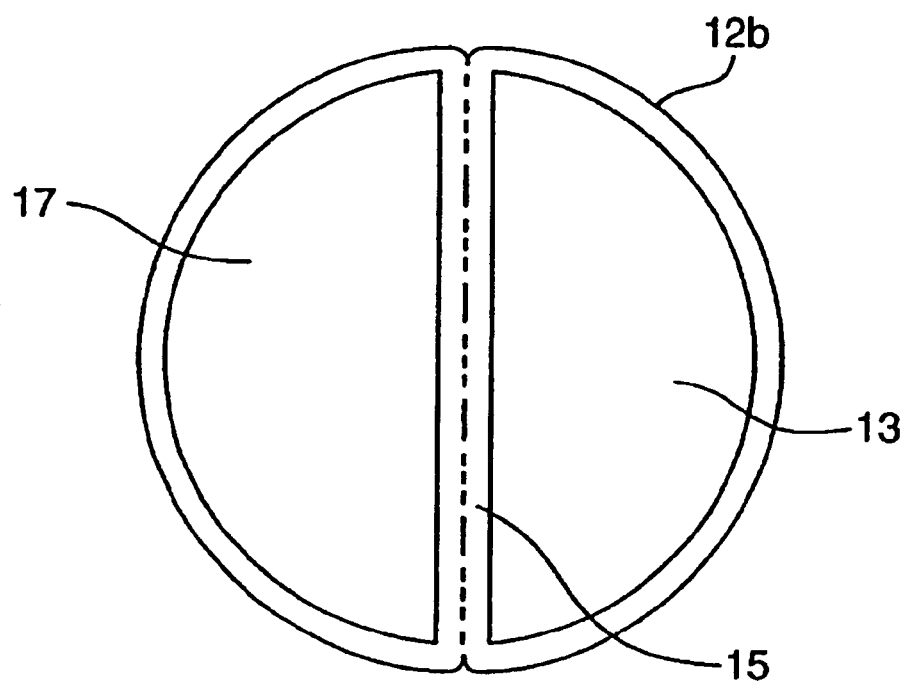
FIG. 4 is a first cross-sectional view of the catheter tube of the multi-lumen catheter of the present invention.
Figure 5:
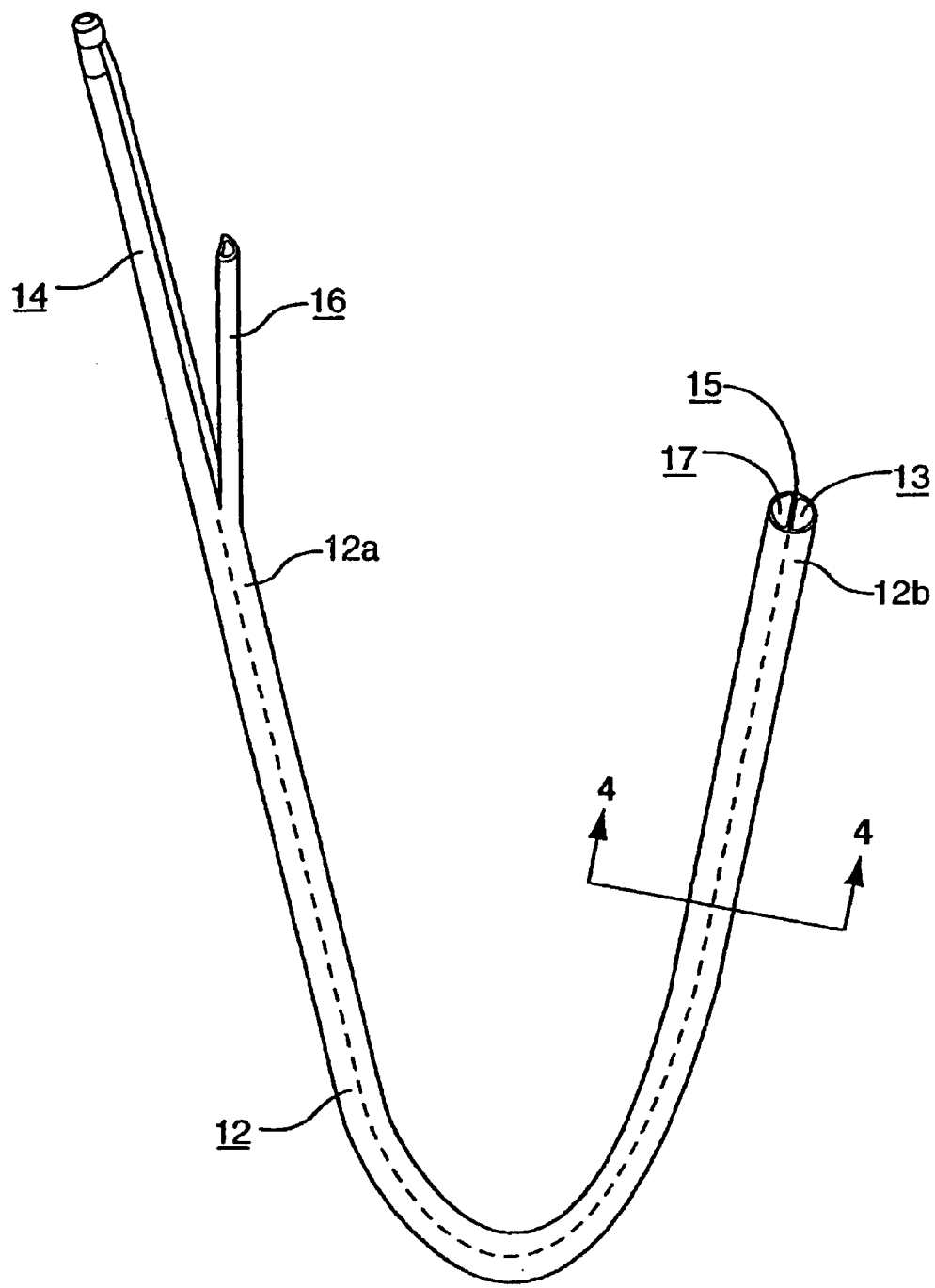
FIG. 5 is an enlarged perspective view of the catheter tube of the present invention.

As shown in FIG. 5, the catheter tube 12 has a first lumen 13 and second lumen 17. Each of the first and second lumen 13, 17 has a generally D-shaped cross-section. A longitudinally extending septum 15 defines each lumen 13, 17 up through the distal portion of the catheter tube 12b, as shown in FIG. 4. Therefore, each lumen 13, 17 connects to a respective cannula 22, 24 for fluid communication therewith.

Preferably, each lumen 13, 17 of the distal portion 12b of the catheter tube 12, and the proximal ends 22a and 24a of the cannulae 22 and 24 are correspondingly marked by an indicator, such as a color, to ensure proper matched correspondence upon connection. To further ensure matched correspondence, preferably tips 14, 16, extension tubes 26, 28 and connectors 30, 32 follow the same marking pattern. Thus, for example, tip 14, the lumen 13, cannula 22, extension tube 26, and connector 30 are marked with a first indicator (e.g., the color blue), while tip 16, lumen 17, cannula 24, extension tube 28, and connector 32 are marked with a second indicator (e.g., the color red). Thus, the first indicator is associated with one of the lumens and a second indicator is associated with the other lumen, such that the first indicator and the second indicator define a correspondence between that lumen and an associated cannula, extension tube, and connector. While the indicator may be a visual indicator such as color, a selectively attachable multi-lumen catheter with any indicator, visual, tactile, or otherwise, should be considered within the scope of the invention.

As described above, the invention is described with a preferred embodiment containing two cannulae and a dual-lumen catheter. The present invention should not be limited, however, to this preferred embodiment and other appropriate configurations should be considered within the scope of the present invention. For example, the catheter tube and corresponding cannulae may be a series of concentric tubes of varying diameter. Alternatively, the assembly 10 may provide a similar configuration to that described hereinabove with three (or more) cannulae and a triple (or more) lumen catheter tube. The preferred embodiment, however, includes two cannulae with a dual-lumen catheter tube.

Preferably, as shown in FIG. 3, the connection between the proximal portions 22a, 24a of the cannulae 22, 24 and the lumens 13 and 17 at the distal portion 12b of the catheter tube 12 is an overlapping fitted connection. However, any other appropriate fastening means, such as detents may be used.

Returning to FIG. 1, an example of a preferred connection between hub body 21 and catheter tube 12 is shown, which includes a connection cover 34 having a proximal portion 34a and a distal portion 34b. Connection cover 34 should fit, and move, axially about the distal portion 12b of the catheter tube 12. The distal end 34b of the connection cover 34 is appropriately threaded such that the connection cover 34 is selectively attachable to the threaded portion 21a of the hub body 21 such that the catheter tube 12 is securely attached to the hub assembly 20. For example, as illustrated in FIG. 1, the connection cover 34 may include female threads to selectively receive the male threads 21a formed on hub body 21.

Figure 6:
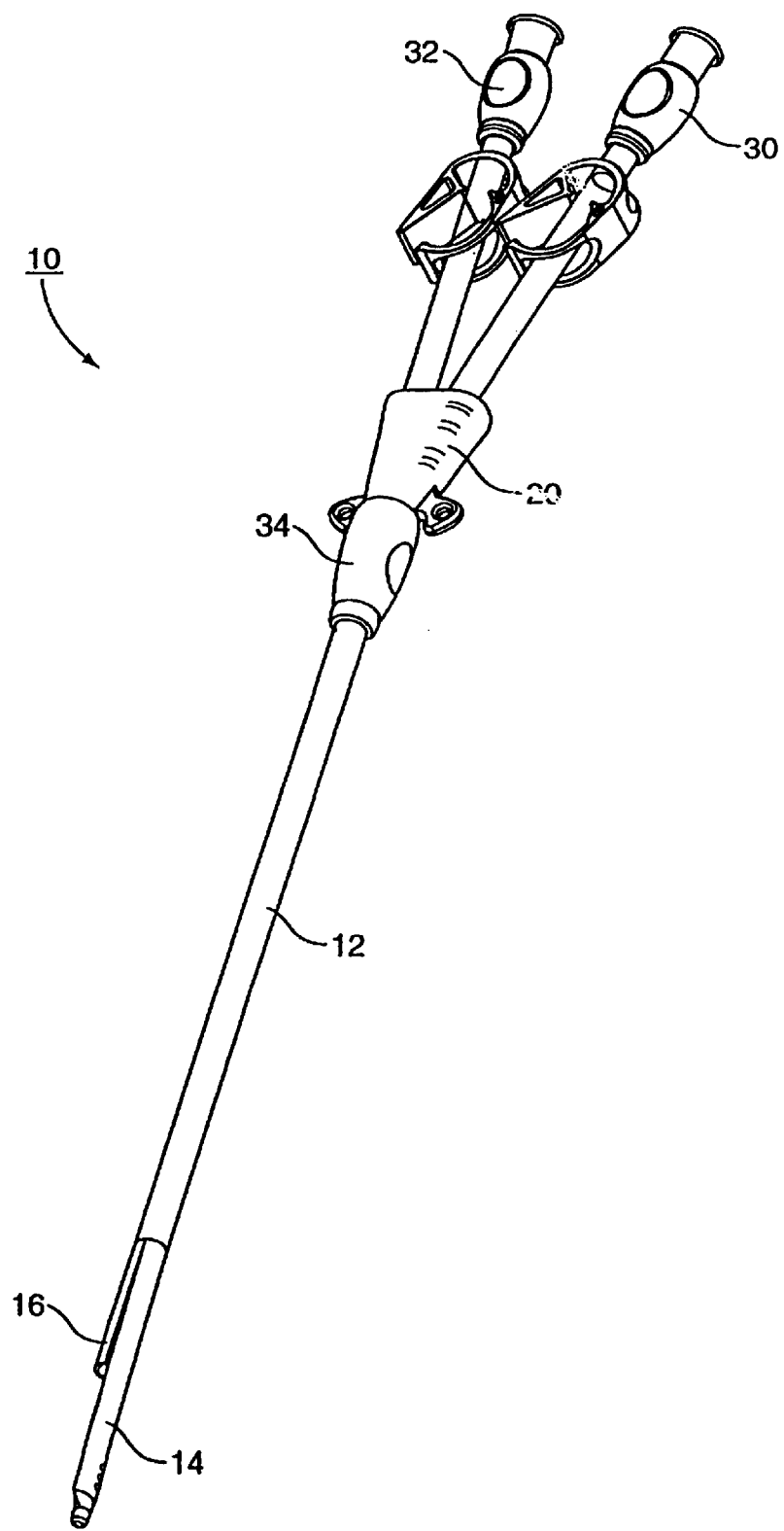
FIG. 6 is a perspective view of an assembled multi-lumen catheter assembly of the present invention.
Figure 7:
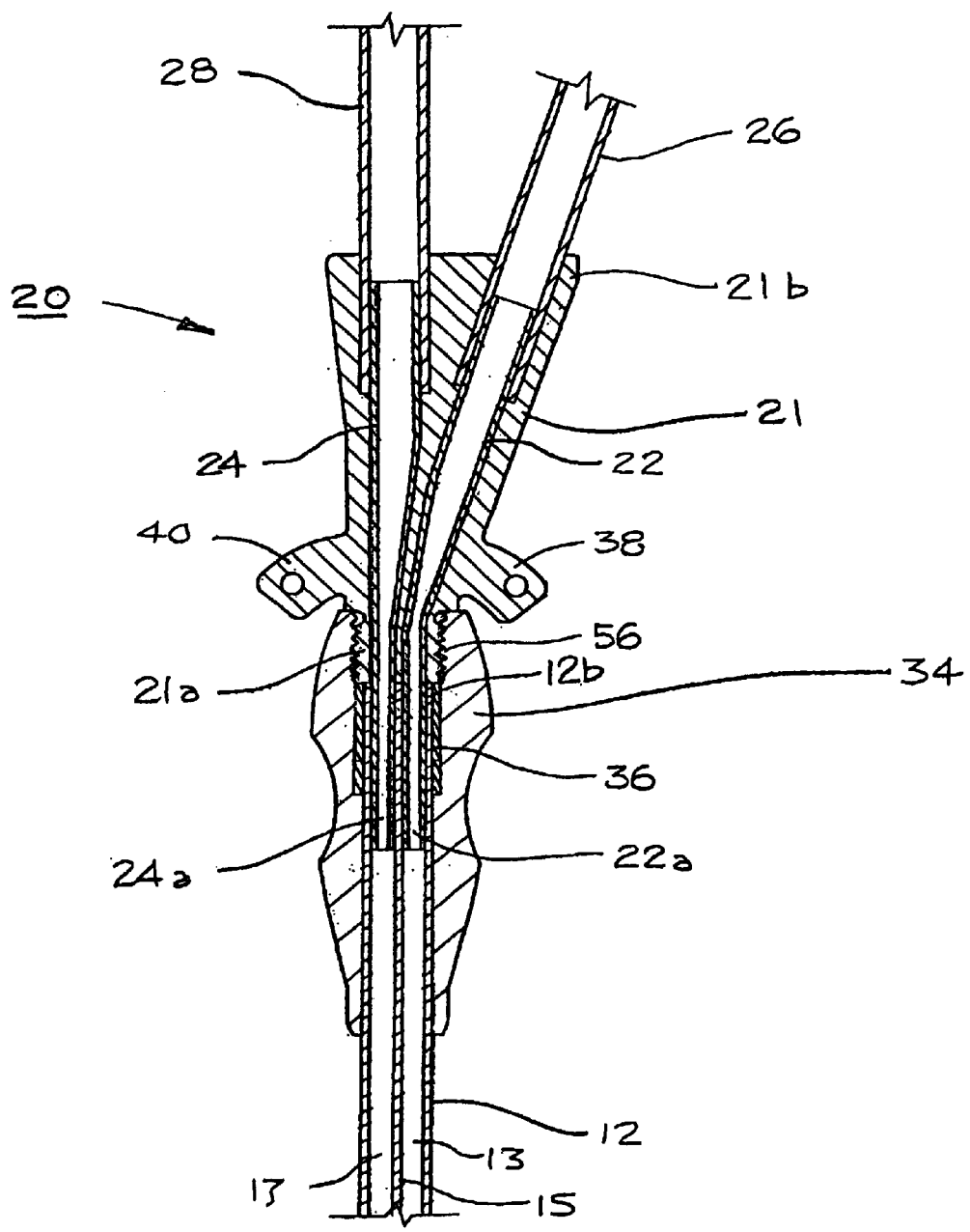
FIG. 7 is a cross-sectional view of the connection and hub areas of the multi-lumen catheter of the present invention.
Figure 8:
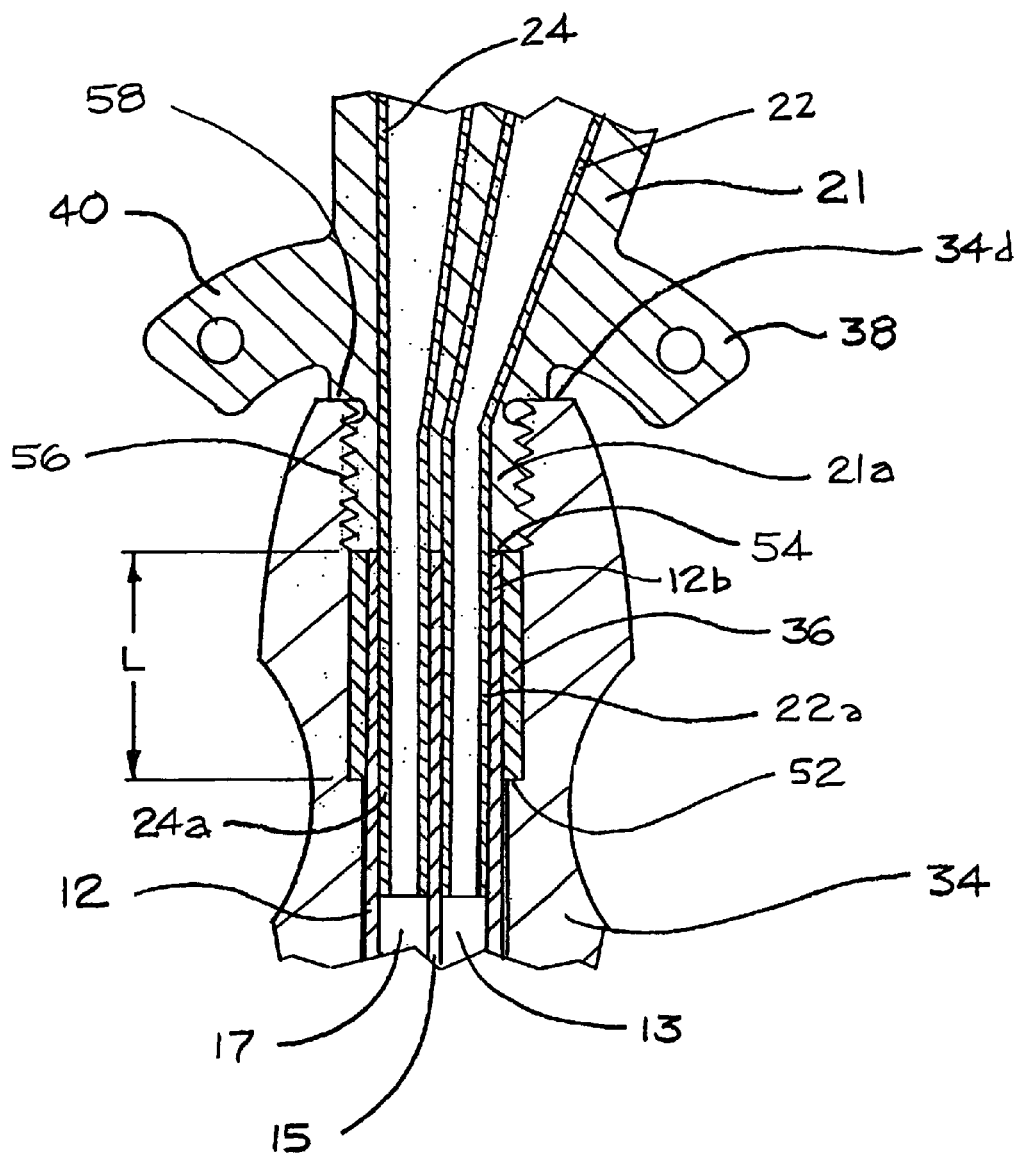
FIG. 8 is an enlarged cross-sectional view of the connection and hub areas of the multi-lumen catheter of the present invention.

Preferably, the present invention also includes a compression sleeve 36 that fits, and moves, axially about the distal portion 12b of the catheter tube 12 as well as fitting and moving axially about the combined proximal portions 22a and 24a of the first and second cannulae 22 and 24. Compression sleeve 36 preferably is formed of malleable material so as to provide further compression about the connection between the cannulae 22 and 24 with the multi-lumen catheter tube 12. The connection cover 34 and the compression sleeve 36 together create force to prevent inadvertent separation of the catheter tube 12 from the hub body 21 after insertion of the catheter tube 12 into a patient. FIG. 6 shows the catheter assembly 10 of the present invention with the hub assembly 20 attached to the catheter tube 12, and FIGS. 7 and 8 show details of the connection. As shown in FIG. 7, the proximal portions 22a, 24a of the first and second cannulae 22, 24 of the hub assembly 20 are inserted into the lumens 13, 17 at the distal end 12b of the catheter tube 12. The compression sleeve 36 is placed about the distal end 12b of the catheter tube 12 in the region engaged with the proximal portions 22a, 24a of the cannulae 22, 24. The threads 56 of the connection cover 34 are engaged on the threads on the proximal portion 21a of the hub body 21. In use, it is preferable to back-fit the connection cover 34 and the connection sleeve 36 over the distal portion 12b of the catheter tube 12 before inserting the proximal portions of the cannulae 22a, 24a into the lumens 13, 17 at the distal end 12b of the catheter tube 12. In this way, the compression sleeve and connection cover 34 are in position to make the connection shown in FIGS. 7 and 8.

As shown in FIG. 8, the connection cover 34 is threadably engaged on the hub body 21 until the distal end 34d of the connection cover 34 seats on the seating surface 58 on the hub body 21. When the connection cover 34 is seated in this way, the compression sleeve 36 is axially compressed by a ledge 52 in the connection cover 34 so that the compression sleeve 36 has a length "L" as shown. Because the compression sleeve 36 has a length in an uncompressed state that is greater than its compressed length "L," the malleable sleeve is caused to exert radially inward pressure on the outer surface of the engaged portion of the catheter tube 12. This radial pressure causes the engaged distal portion 12b of the catheter tube 12 to tightly grip the engaged proximal portions 22a, 24a of the cannulae 22, 24, thereby creating substantial frictional resistance to extraction of the cannulae 22, 24 from the catheter tube 12, and thereby creating a substantially leak-tight seal between the cannulae 22, 24 and the catheter tube. Preferably, the connection cover 34 is screwed onto the proximal portion 21a of the hub body 21 sufficiently tightly such that the frictional engagement between the distal end 34d of the connection cover 34 and the seating surface 58 of the hub body 21 is sufficient to resist inadvertent loosening of the connection cover 34 during use. As can be appreciated from FIG. 8, an advantage of this connector construction is that the diameter of each of the lumens 13, 17 remains constant throughout the connection area, even though there is inward radial pressure exerted on the catheter tubes 12, 15 that define the lumens. It is important that the diameters of the lumens remain constant throughout the connection area because any reduction of the lumen diameter will restrict flow, which will result in less than optimal performance.

To remove the catheter tube 12 from the hub assembly 20, the compression cover 34 is unscrewed from the proximal portion 21a of the hub body, thereby permitting the compression sleeve 36 to return to a relaxed, uncompressed state. The cannulae 22a, 24a can then be withdrawn from the catheter tube 12 without substantial frictional resistance.

A preferred method for inserting into a patient the catheter assembly 10 of the present invention requires the following: a multi-lumen catheter tube 12 with, preferably, tapered silicone tips 14, 16, and, as are known in the art, an introducer needle, multiple tear away sheath dilator introducers, J-flex guidewires, trocars, lock right adapters with clamps, injection caps, a scalpel, sutures, and adhesive wound dressing. Additionally, the physician should have access to scissors, forceps, needles dish, syringes and gauzes.

A preferred method for insertion of the catheter of the present invention into a patient's jugular vein begins with placing the patient in a position with the patient's head turned to the opposite side of where the jugular vein is to be cannulated. The anatomical landmark for proper insertion is defined by the triangle formed by the lateral edge of the sternal head, the medial edge of the clavicular head of the steocleidomastoid muscle, and the upper edge of the clavicle.

The patient's neck and a portion of the patient's thorax beneath the clavicle, preferably at least about 20 centimeters (cm), should be appropriately prepared for incision. Thereafter, the patient should be draped and local anesthetic should be administered.

Preferably, a skin wheel should be created, taking care to infiltrate the subcutaneous tissue for about 2 to 3 cm. Next, preferably with an 18-gauge needle attached to a syringe, the physician should identify the internal jugular vein by aspiration and then proceed at an angle while continuing to aspirate with the syringe. Once the internal jugular vein has been located, the preferred method includes detaching the syringe while leaving the needle in place. The needle opening should then be occluded and thereafter the J-flex guidewire should be introduced through the needle and into the internal jugular vein. The guidewire should pass without resistance into the exact position. The needle should be removed, thus leaving the guidewire in place. The guidewire should rest at the junction of the superior vena cava and the right atrium. Appropriate guidewire placement can be confirmed with fluoroscopy.

Next, with a scalpel, the physician should make an incision in the skin that is wide enough for the catheter tube 12 to pass. A tearaway sheath dilator may be introduced over the guidewire and into the vein far enough to dilate the vessel. After expanding the vein wall, the guidewire may be removed while occluding the dilator opening. A trocar should be screwed onto the catheter tube 12 by turning the trocar clockwise, but not the catheter tube 12. Turning the catheter tube 12 may cause it to kink. The dilator may be removed, leaving the tearaway sheath in place to introduce the catheter tube 12, again being careful to occlude the sheath opening. As the catheter tube 12 is fed into the sheath the tearaway sheath may be torn away. Care should be taken that the catheter tube 12 does not back out of the vessel.

Air embolus is avoided by the patient's positioning described above, and also by asking the patient to inhale deeply and then hold their breath. At this point, fluoroscopy should be performed to confirm catheter tube 12 placement. The tip 14 of the venus catheter should reach the opening of the right atrium and the tip 16 of the arterial catheter should be approximately 4 cm higher. As described above, proper positioning is important. Positioning, as described, is believed to prevent blood recirculation during hemodialysis.

Next, a tunnel, of about 8 to 10 cm, should be created in a caudal and internal direction by means of the tunneler, which may be shaped to physician preference. The catheter tube 12 should be gently pulled through the tunnel until the loop at the original puncture site is gone. When correctly inserted, the catheter tube 12 should rest over the clavicle. Care should be taken to avoid excessive force, as this may cause the catheter tube 12 to separate from the tunnel. Preferably, the method includes surveying this area to ensure there are no kinks in the catheter tube 12 and there is a smooth turn.

Next, while pinching the distal portion 12*b* of the catheter tube 12, the hub assembly 20 is attached to the catheter tube 12. The connector 34 is backfit over the catheter tube 12. Next, the compression sleeve 36 is backfit over the catheter tube 12. The proximal portions 22*a*, 24*a* of cannulae 22, 24 are inserted into lumens 13 and 17, respectively, creating a friction fit. Preferably, the cannulae 22, 24, or the corresponding extension tubes 26, 28 or the corresponding connectors 30, 32 are marked so that the cannulae 22, 24 are inserted into the correct lumens 13, 17.

After backfiting the connector cover 34 and the compression sleeve 36 over the catheter tube 12, the compression sleeve 36 is slid into a position that is approximately adjacent to the threaded portion 21*a* of the hub body 21. Finally, the connector cover 34 is attached to the hub body 21 by turning the connector cover 34 so that the female threaded portion of the connector cover 34 receives the male threaded portion 21*a* of the hub body 21 thereby creating a secure attachment of the hub assembly 20 to the catheter tube 12. Clamps 42, 44 may be used with extension tubes 26, 28.

The extension tubes 26, 28 should be filled with 3 to 4 cc of 5000 units of heperinized saline, clamped, and attached with the injection cap. X-rays should again be performed to reconfirm placement. The small incision is closed with sutures. The patient is now ready for dialysis.

Preferably, the catheter tube 12 is formed with radioopaque silicone, to facilitate visualization under fluoroscopy.

Although specific embodiments of the present invention have been illustrated and described in detail, it is to be expressly understood that the invention is not limited thereto. The above detailed description of the embodiment is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A selectively attachable hub assembly for reversible sealable connection with a multi-lumen catheter, the hub assembly comprising:
   (a) a hub body having a proximal end portion and distal end; the proximal end portion including a plurality of threads;
   (b) first and second cannulae outwardly extending from the proximal end portion of the hub body;
   (c) first and second extension tubes outwardly extending from the distal end of the hub body, the first and second extension tubes being in fluid communication with the first and second cannulae, respectively, and including distal ends;
   (d) first and second connectors configured for connecting the distal ends of the first and second extension tubes to a fluid exchange device;
   (e) a substantially cylindrical compression sleeve; and
   (f) a connection cover having a proximal end, a distal end, and a central bore therethrough, the central bore including a plurality of threads proximate to the distal end of the connection cover and a compression sleeve compression ledge located between the proximal end and the distal end of the compression cover, wherein the connection cover threads are matable with the threads on the proximal portion of the hub body a distal end of the multi-lumen catheter is disposed over the cannulae and the connection cover and compression sleeve are disposed over the distal end of the multi-lumen catheter, the threads of the connection cover are revesibly engaged with the threads of the hub body and the compression sleeve is compressed between the compression ledge and the hub body.

2. The hub assembly of claim 1, wherein the first and second extension tubes extend outwardly from the distal end of the hub body at an included angle of about 15 degrees.

3. The hub assembly of claim 1, wherein the first and second cannulae extending outwardly from the proximal end portion of the hub body have substantially D-shaped cross sectional shapes.

4. The hub assembly of claim 1 further comprising:
   a first indicator associated with the first cannula, the first extension tube, and the first connector; and
   a second indicator associated with the second cannula, the second extension tube, and the second connector;
   wherein the first indicator and the second indicator define a matching correspondence between the the cannulae, the extension tubes, and the connectors.

5. A multi-lumen catheter assembly having a selectively attachable hub, the catheter assembly comprising:
   (a) a multi-lumen catheter tube having a proximal portion and a distal portion and a hub assembly having a proximal portion and a distal portion, wherein the distal portion of the catheter tube is selectively attachable to the proximal portion of the hub assembly after subcutaneous insertion of the proximal portion of the catheter tube into a patient;
   (b) a first cannula and a second cannula, wherein each of the cannulae has a proximal portion and a distal portion, the proximal portion of the first cannula being connectable with the first lumen of the catheter tube, and the proximal portion of the second cannula being connectable with the second lumen of the catheter tube, to provide for fluid communication therebetween;
   (c) a first extension tube and a second extension tube, wherein each of the extension tube has a proximal portion and a distal portion, and wherein the proximal portion of the first extension tube is connectable with the distal portion of the first cannula, and the proximal portion of the second extension tube is connectable with the distal portion of the second cannula, to provide fluid communication therebetween;
   (d) a first connector and a second connector, the first connector being securely attached to the distal portion of the first extension tube and the second connector being securely attached to the distal portion of the second extension tube, wherein each of the connectors are attach able to a fluid conveying device to provide fluid flow between the hub assembly and the catheter tube;

(e) a hub body formed about the connection between the proximal portion of each extension tube with the distal portion of each cannula, the hub body including a proximal portion including a plurality of threads;

(f) a connection cover having a proximal end, a distal end, and a central bore therethrough, the central bore including a plurality of threads proximate to the distal end of the connection cover and a ledge located between the proximal end and the distal end, wherein the cover fits and moves axially about the distal portion of the catheter tube and the internal threads are matable with the threads of the proximal portion of the hub body; and (g) a compression sleeve, the compression sleeve fitting and moving axially about the distal portion of the catheter tube and the proximal portion of the first and second cannulae;

wherein the threads proximate to the distal end of the connection cover are selectively connectable to the threads on the proximal portion of the hub assembly, and the ledge in the bore of the connection cover imparts axial compression to the compression sleeve when the connection cover is fully engaged with the proximal portion of the hub body, hereby imparting inward radial compression of the distal portion of the catheter tube, and hereby forming tight sealable engagement between the hub assembly and the catheter tube.

6. The multi-lumen catheter of claim 5, wherein the angle between the first cannula and the second cannula is about 15 degrees.

7. The multi-lumen catheter of claim 5, wherein the proximal portion of the catheter tube further comprises a first and second lumen, each of the first and second lumens having a generally D-shaped cross-section, wherein each of the first and second lumens transition toward the distal portion of the catheter tube into a single lumen having a longitudinally extending septum.

8. The multi-lumen catheter of claim 5, further comprising:

a first indicator associated with a first lumen, the first cannula, and the first connector; and a second indicator associated with a second lumen, the second cannula, and the second connector;

wherein the first indicator and the second indicator define a matching correspondence between the lumens, the cannulae, and the connectors.

9. A selectively attachable hub assembly for sealable connection with a multi-lumen catheter, the hub assembly comprising:

a. a hub body having a proximal end and distal end;

b. a plurality of cannulae extending from the proximal end of the hub body;

c. a plurality of extension tubes extending from the distal end of the hub body, each extension tubes being in fluid communication with each cannulae, and each extension tube including a distal end;

d. a connector attached to each extension tube distal end;

e. a compression sleeve; and f. a connection cover having a proximal end, a distal end, and a central bore therethrough, the central bore including compression ledge located between the proximal end and the distal end of the compression cover; the compression sleeve sized to fit inside the central bore of the connection cover;

the connection cover and compression sleeve are disposed over a distal end of the multi-lumen catheter, the connection cover is removeably attached to the proximal end of the hub body and the catheter removeably engages the cannulae of the hub body; the compression sleeve is compressed between the hub body and the compression ledge and the multi-lumen catheter is sealed to the hub assembly.

10. The multi-lumen catheter of claim 9, wherein the extension tubes extend from the distal end of the hub body at an included angle of about 15 degrees.

11. The multi-lumen catheter of claim 9, wherein the cannulae have substantially D-shaped cross sectional shapes.

12. The multi-lumen catheter of claim 9 further comprising:

a. a first indicator associated with at least one extension tube; and b. a second indicator associated with at least one extenstion tube different from the first extension tube.

13. The multi-lumen catheter of claim 9, wherein the hub body further comprising a proximal portion including connection threads and the connection cover further comprising, proximate to the distal end thereof, connection threads that are selectively connectable to the hub assembly connection threads.

\* \* \* \* \*